Figure 1:
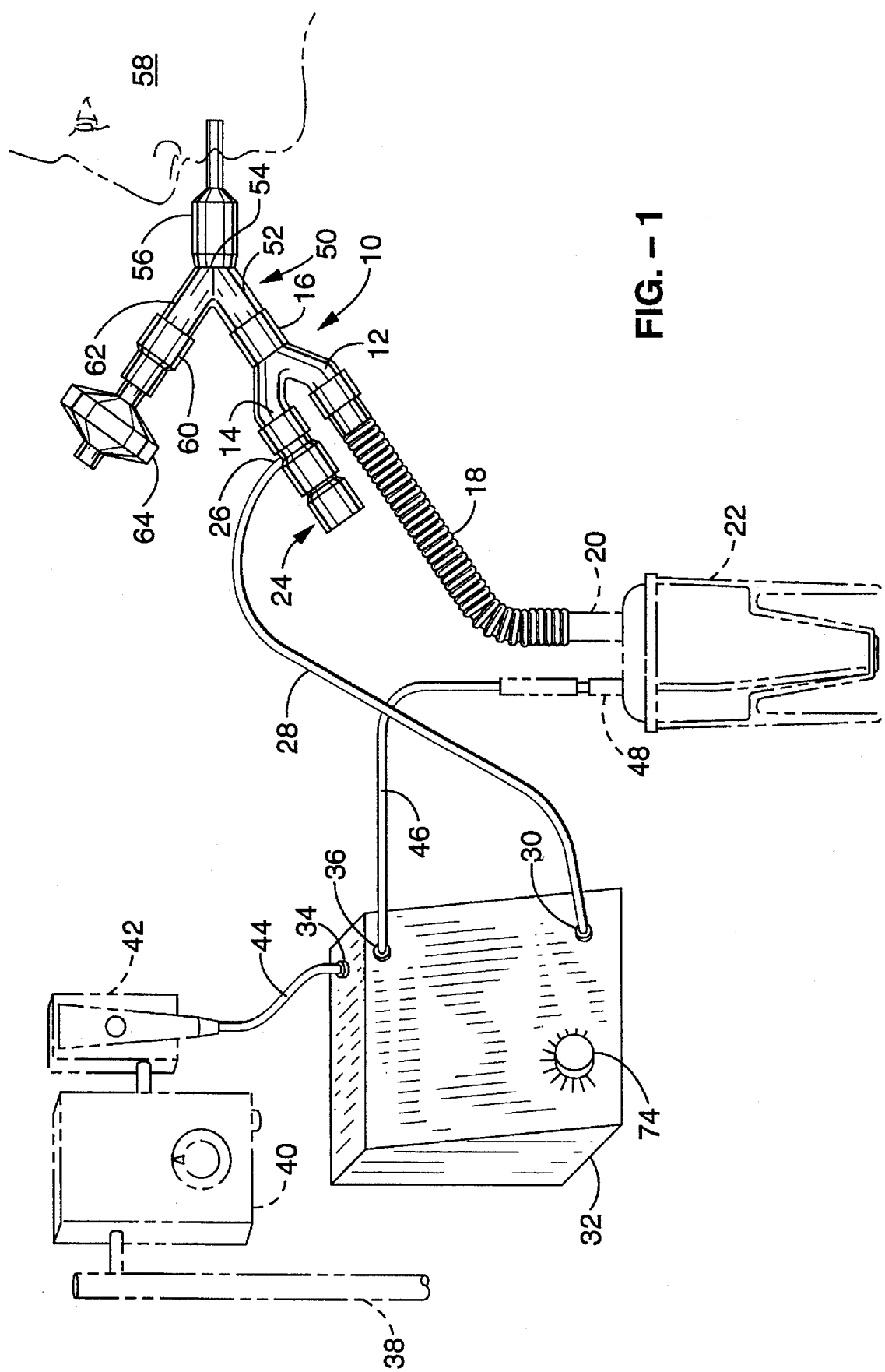

United States Patent [19]
Piper et al.

[11] Patent Number: 5,479,920
[45] Date of Patent: Jan. 2, 1996

[54] BREATH ACTUATED MEDICINAL AEROSOL DELIVERY APPARATUS

[75] Inventors: Samuel D. Piper; James I. C. Lee; Gordon A. Wong, all of Sacramento, Calif.

[73] Assignee: Vortran Medical Technology, Inc., Sacramento, Calif.

[21] Appl. No.: 205,598

[22] Filed: Mar. 1, 1994

[51] Int. Cl.$^6$ ........................................... A61M 16/00
[52] U.S. Cl. ............................ 128/204.23; 128/204.18; 128/203.12
[58] Field of Search .................. 128/204.21, 200.14, 128/204.26, 205.14, 203.12, 203.28, 200.21, 204.18, 204.23

[56] References Cited

U.S. PATENT DOCUMENTS

| | | | |
|---|---|---|---|
| 3,083,707 | 4/1963 | Sealer | 128/200.14 |
| 3,662,751 | 5/1972 | Barkalow et al. | 128/204.26 |
| 3,769,973 | 11/1973 | Esbenshade, Jr. | 128/200.14 |
| 4,106,503 | 8/1978 | Rosenthal | 128/194 |
| 4,206,754 | 6/1980 | Cox et al. | 128/204.26 |
| 4,391,271 | 7/1983 | Blanco | 128/203.12 |
| 4,448,192 | 5/1984 | Stawitcke et al. | 128/204.26 |
| 4,529,003 | 7/1985 | Iannuzzeli | 128/200.14 |
| 4,660,547 | 4/1987 | Kremer, Jr. et al. | 128/200.21 |
| 4,677,975 | 7/1987 | Edgar et al. | 128/200.14 |
| 4,782,828 | 11/1988 | Burnett | 128/200.14 |
| 4,819,629 | 4/1989 | Jonson | 128/200.14 |
| 4,823,784 | 4/1989 | Bordoni et al. | 128/200.14 |
| 4,832,012 | 5/1989 | Raabe et al. | 128/200.21 |
| 5,020,530 | 6/1991 | Miller | 128/200.21 |
| 5,050,593 | 9/1991 | Poon | 128/204.23 |
| 5,080,093 | 1/1992 | Raabe et al. | 128/203.12 |
| 5,322,057 | 6/1994 | Raabe et al. | 128/203.12 |
| 5,323,772 | 6/1994 | Linden et al. | 128/204.23 |
| 5,373,842 | 12/1994 | Olsson et al. | 128/204.26 |

*Primary Examiner*—Edgar S. Burr
*Assistant Examiner*—V. Srivastava
*Attorney, Agent, or Firm*—John P. O'Banion

[57] ABSTRACT

An apparatus for delivering medicinal aerosol on-demand during patient inhalation wherein delivery of aerosol from a nebulizer (22) is optimized by synchronizing delivery to the inspiration of a patient (58) is disclosed. A control unit (32) monitors airway pressure and controls the flow of gas so that aerosol delivery is triggered by patient inhalation, in which event delivery continues for a predetermined time period which is adjustable by the user. The apparatus can be used with a mouthpiece (56), a face mask (66) without an integral exhalation valve, or a face mask (68) with an integral exhalation valve. The apparatus significantly increases the efficiency of delivery of medicinal aerosol by sensing a patient's inhalation and exhalation cycles and delivering aerosol only after a certain inhalation pressure is sensed following a certain previous exhalation pressure. These pressures, which are compared against predetermined thresholds, correspond to the actual patient breathing condition. By monitoring the patient's inhalation and exhalation in this manner, aerosol delivery is synchronized with the patient's breathing pattern. In this way, the apparatus prevents aerosol contamination of the environment without requiring an exhalation filter since aerosol is delivered to the patient only during inhalation. Exhalation is not obstructed since aerosol is not delivered during exhalation. Further, when it is desirable to use an exhalation filter to reduce the amount of exhalation gas discharged into the environment, the apparatus reduces occlusion occurring in the exhalation filter.

12 Claims, 3 Drawing Sheets

BREATH ACTUATED MEDICINAL AEROSOL DELIVERY APPARATUS

BACKGROUND OF THE INVENTION

1. Field of the Invention

This invention pertains generally to delivery of medicinal aerosols for inhalation therapy, and more particularly to an apparatus for delivering medicinal aerosols to a patient on demand during inhalation.

2. Description of the Background Art

It is known that the thin membrane of the lungs can be easily penetrated by medicinal aerosols and provides a convenient and generally safe vehicle for obtaining rapid absorption of medication by the body. Medication or drugs are generally delivered to the lung membrane in the form of a fine mist or aerosol which is breathed into the lungs through the nose or mouth of the patient. Quite typically, a nebulizer is used to convert a liquid into a fine aerosol, and the aerosol is introduced into the lungs by means of a mouthpiece which delivers the aerosol through the mouth only, or by means of a face mask which delivers the aerosol through both the mouth and nose of the patient. However, conventional delivery systems provide a continuous flow of aerosol and, as a result, a portion of the aerosol is wasted during exhalation of the patient. Furthermore, the wasted medicinal aerosol is exhausted into the ambient air, thereby creating environmental risks as well as risking the health and safety of health care workers who breath the surrounding air. Also, bacteria and other materials present in the patient's exhalation gas are permitted to escape. Heretofore, inhalation booths or tents with laminar flow hoods and filtration systems have been used to guard against those risks. However, such devices are expensive and bulky, and still do not protect the health care workers who must enter the tent or hooded area.

Various such inhalation devices have been previously developed. For example, U.S. Pat. No. 4,823,784 issued to Bordoni et al. on Apr. 25, 1989, discloses an aerosol inhalation apparatus which runs continuously and does not provide for synchronization of delivery with the patient's breathing cycle. Further, the device requires use of a filter to remove or reduce the amount of unused aerosolized medicament discharged into the ambient air. The filter provides a flow restriction thereby impeding exhalation and increasing discomfort, and is subject to occlusion from fluids in the exhalation gas. U.S. Pat. No. 4,106,503 issued to Rosenthal et al. on Aug. 15, 1978, discloses a metering system for stimulating bronchial spasm which delivers a metered dose of nebulized antigen during inhalation but must be manually activated with a switch. U.S. Pat. No. 4,677,975 issued to Edgar et al. on Jul. 7, 1987, discloses a method and apparatus for dispensing inhalable material which tells the patient when to inhale or exhale based on timed intervals and delivers the inhalable material during inhalation. The device does not administer medicament in synchronization with a normal breathing cycle. U.S. Pat. No. 5,080,093 issued to Raabe et al. on Jan. 14, 1992 and U.S. Pat. No. 4,832,012 issued to Raabe et al. on May 23, 1989, disclose intermittent signal actuated nebulizers in which electrical signals from a respirator device are sensed and used to trigger delivery of medicinal aerosol.

As can be seen, therefore, a need exists for an aerosol delivery apparatus which initiates delivery of medicine only at the beginning of the inhalation cycle, and which prevents delivery of medicine during the exhalation cycle. The present invention satisfies that and other needs, and overcomes the deficiencies in devices heretofore developed.

SUMMARY OF THE INVENTION

The present invention generally pertains to an apparatus for delivering medicinal aerosol on demand during patient inhalation wherein delivery of aerosol from a nebulizer is optimized by synchronizing delivery to the inspiration of a patient. Through the use of one-way valves, a breathing circuit monitors airway pressure and controls the flow of gas so that aerosol delivery occurs only during inhalation. Furthermore, by monitoring airway pressure and delivering aerosol only during inhalation, the percentage of medicinal aerosol that is delivered to the patient is increased, and aerosol contamination of the surrounding air is prevented. Additionally, the unidirectional feature of the breathing circuit allows an exhalation filter to be used to minimize the risk of exposure of health care workers or family members to contaminants contained in the patient's exhalation gas.

By way of example, and not of limitation, a breath actuated aerosol delivery apparatus in accordance with the present invention includes a patient wye, one leg of which is coupled to an aerosol supply conduit and the other leg of which is coupled to a one-way inhalation valve. The outlet of the wye is then coupled directly to a face mask having a one-way exhalation port or, alternatively, coupled to one leg of a second wye having an outlet which is in turn coupled to a mouthpiece or a face mask which does not have an exhalation port. The other end of the aerosol supply conduit is coupled to the aerosol outlet of a nebulizer.

The inhalation valve includes a signalling means in the form of a pressure monitor port which is in turn coupled to the pressure monitoring input of a control unit by means of a pressure tube or, alternatively, a flow sensing device is employed as a signalling means. The control unit also includes a gas supply inlet which is coupled to a pressurized supply of breathable gas, and a gas supply outlet which is coupled to the gas supply inlet of the nebulizer through a hose. In a home situation where a pressurized supply of breathable gas is not available, the control unit can include an internal compressor for using ambient air as a gas supply to the nebulizer.

During patient inhalation, the one-way inhalation valve opens and the pressure at the pressure monitor port drops to a negative pressure (below atmospheric), or a differential pressure is sensed across the flow sensing device. This drop in pressure is sensed by the control unit and, in turn, the control unit directs breathable gas to be fed to the nebulizer for a period of time (charging period) which is adjustable to deliver aerosol during the entire inhalation cycle or for shorter periods of time if smaller doses are desired. The breathable gas causes the medicine in the nebulizer to be aerosolized, and the medicinal aerosol is inhaled by the patient. During exhalation of the patient, the exhalation gases cause the inhalation one-way valve to close, and the pressure at the pressure monitor port rises to a positive pressure above ambient which signals the beginning of patient exhalation.

If a face mask with one or more exhalation ports is used, the exhalation gases are vented to the atmosphere during exhalation. In the configuration wherein a mouthpiece or a face mask without an exhalation port is used, the exhalation gases are vented through a one-way exhalation valve coupled to the remaining leg of the second wye. To prevent contamination of the atmosphere from exhaled medicine or bacteria, a filter can be coupled to the outlet of the exhalation valve.

The present invention further significantly increases the efficiency of delivery of medicinal aerosol by sensing a patient's inhalation and exhalation cycles and delivering aerosol only after a certain inhalation pressure is sensed following a certain previous exhalation pressure. These pressures, which are compared against predetermined thresholds, correspond to the actual patient breathing condition. By monitoring the patient's inhalation and exhalation in this manner, aerosol delivery is synchronized with the patient's breathing pattern.

The present invention prevents aerosol contamination of the environment without requiring an exhalation filter since aerosol is delivered to the patient only during inhalation. Further, since the nebulizer does not operate during patient exhalation, there is no obstruction to exhalation flow as there is in devices where the nebulizer operates continuously. Thus, the present invention will not damage the patient's lungs since it does not obstruct exhalation. Additionally, the present invention reduces the risk of occlusion in an exhalation filter when used. In conventional devices, filter occlusion blocks patient exhalation.

Accordingly, an object of the invention is to prevent aerosol waste.

Another object of the invention is to prevent aerosol contamination of environment without the need for an exhalation filter.

Another object of the invention is to deliver medicinal aerosol on demand.

Another object of the invention is to deliver medicinal aerosol only during patient inhalation.

Another object of the invention is to optimize delivery of medicinal aerosol to a patient.

Another object of the invention is to provide a breath actuated aerosol delivery apparatus which can be used in conjunction with either a mouthpiece or a face mask.

Another object of the invention is to reduce the occlusion rate of an exhalation filter.

Another object of the invention is to provide a breath actuated aerosol delivery apparatus which can be used in conjunction with an exhalation filter when needed.

Another object of the invention is to activate a nebulizer once during an inhalation/exhalation cycle.

Another object of the invention is to make nebulizer treatment easier and more convenient.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 1 is a schematic representation of the aerosol delivery apparatus of the present invention shown configured for use in conjunction with a mouthpiece.

FIG. 2 is a schematic representation of the aerosol delivery apparatus of FIG. 1 shown configured for use in conjunction with a face mask without an integral exhalation valve.

FIG. 3 is a schematic representation of the aerosol delivery apparatus of FIG. 1 shown configured for use in conjunction with a face mask having an integral exhalation valve.

DESCRIPTION OF THE PREFERRED EMBODIMENTS

Referring more specifically to the drawings, for illustrative purposes the present invention is embodied in the apparatus which is generally shown in FIG. 1 through FIG. 3, and its method of use. It will be appreciated that the apparatus may vary as to configuration and as to details of the parts without departing from the basic concepts as disclosed herein, and that the method of use may vary as to its steps and their order of implementation without departing from the basic concepts as disclosed herein.

Referring to FIG. 1, the present invention includes a conventional wye fitting 10 or the like which has a first leg 12 which serves as an aerosol inlet port, a second leg 14 which serves as an air inlet port, and an outlet 16 which serves as an aerosol outlet port. One end of an aerosol supply conduit 18 is coupled to first leg 12; the other end of aerosol supply conduit 18 includes conventional means for coupling to the aerosol outlet 20 of a conventional nebulizer 22 or the like. A one-way (unidirectional) inhalation valve 24, which is a conventional flapper valve or the like wherein the valve opens to permit flow in one direction but closes to prevent flow in the other direction, is coupled to second leg 14. In the present invention, inhalation valve 24 permits ambient air to be drawn into second leg 14 during inhalation but closes during patient exhalation. In this manner, when the patient exhales, inhalation valve 24 closes and pressure builds up within the breathing circuit to a level above atmospheric pressure due to the resistance across the exhalation circuitry in the breathing circuit. Similarly, when the patient inhales, valve 24 opens and pressure in the breathing circuit drops to a level below atmospheric pressure.

To take advantage of this change in pressure, inhalation valve 24 includes a pressure monitor port 26 to which one end of a pressure tube 28 is coupled as an inhalation/exhalation signalling means. The other end of pressure tube 28 is configured for coupling to a pressure monitoring input 30 of a control unit 32. Those skilled in the art will appreciate that pressure monitor port 26 could be located at any other position in the circuit where a change in pressure resulting from a transition between patient inhalation and patient exhalation can be sensed. Alternatively, a flow sensing device could be employed between inhalation valve 24 and first leg 52 of second wye fitting 50 as a pressure signalling means instead of using pressure monitor port 26 to detect pressure changes. In that event, a differential pressure would indicate a change in flow and, therefore, be indicative of patient inhalation or patient exhalation. As can be seen, therefore, there is provided a signaling means for signaling patient inhalation and patient exhalation, with signals being generated by the patient's actual inhalation flow and the patient's actual exhalation flow, respectively.

Control unit 32 also includes a gas supply inlet 34 and a gas supply outlet 36, both of which are compatible with compressed gases such as oxygen. Preferably, gas supply inlet 34 includes a male oxygen DISS type fitting (not shown) for coupling to a breathable gas line 38 through an oxygen blender 40, flow meter 42 and first gas supply tube 44, which are of conventional types used in inhalation therapy and which do not constitute elements of this invention. Gas supply outlet 36 preferably includes a quick-disconnect fitting (not shown) which is turn coupled to one end of a second gas supply tube 46, the other end of which is configured for coupling to a gas inlet 48 on nebulizer 22.

A second wye fitting 50, which is also a conventional fitting or the like, is coupled to wye fitting 10 by coupling first leg 52, which serves as an aerosol inlet port, to outlet 16 as shown. Outlet 54, which serves as an aerosol outlet port, is coupled to a mouthpiece 56 which is inserted into the mouth of a patient 58, and a one-way (unidirectional) exhalation valve 60 is coupled to second leg 62 which serves as an exhalation gas outlet port. Similar to inhalation valve 24, exhalation valve 60 comprises a conventional flapper valve or the like wherein the valve opens to permit flow in one direction but closes to prevent flow in the other direction. In the present invention, exhalation valve 60 opens to permit exhalation gases to be vented during exhalation but closes during inhalation. Additionally, a filter 64 can be coupled to exhalation valve 60 for purposes of preventing medicine and bacteria present in the exhalation gases from entering the ambient air.

Figure 2:
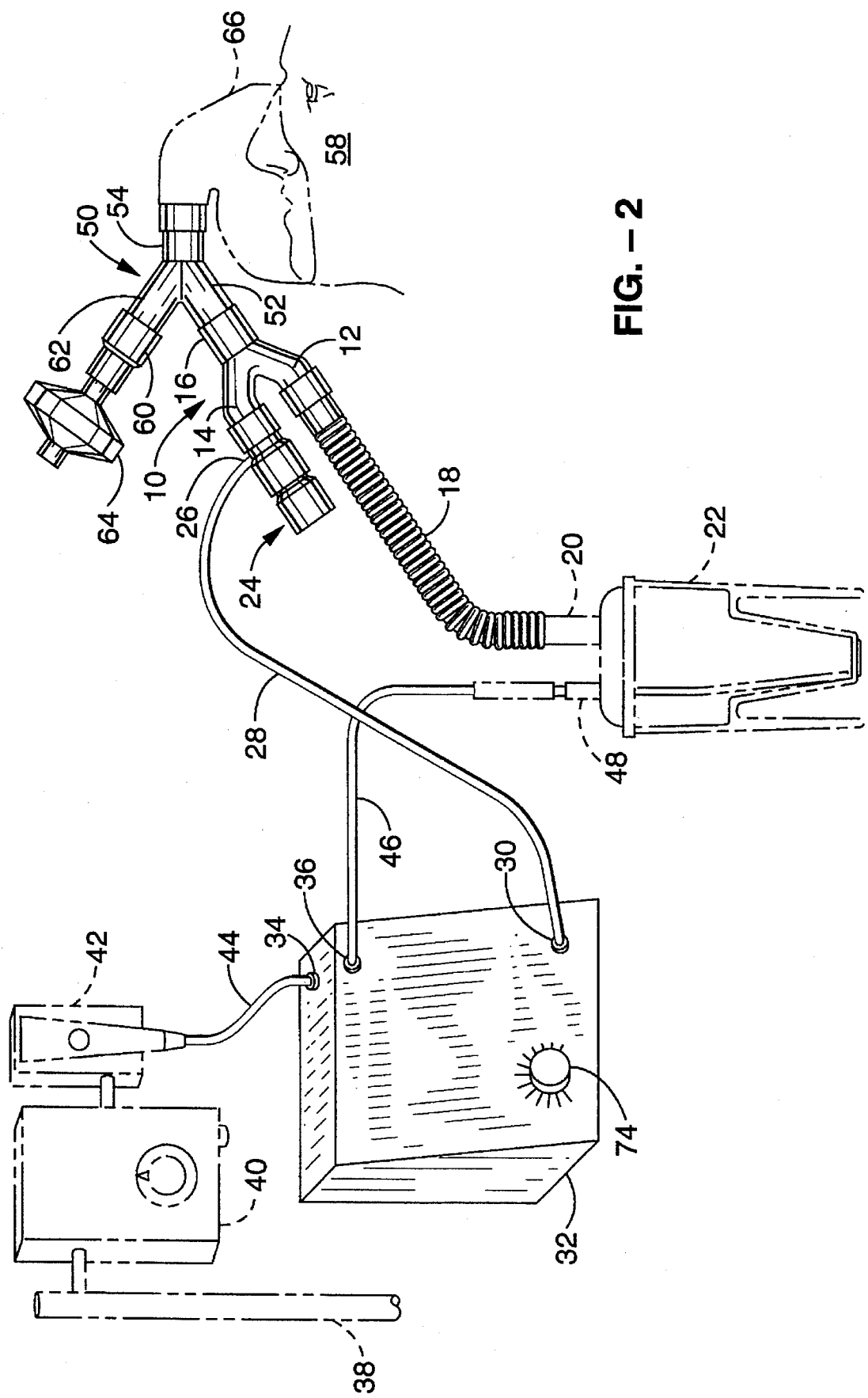
Figure 3:
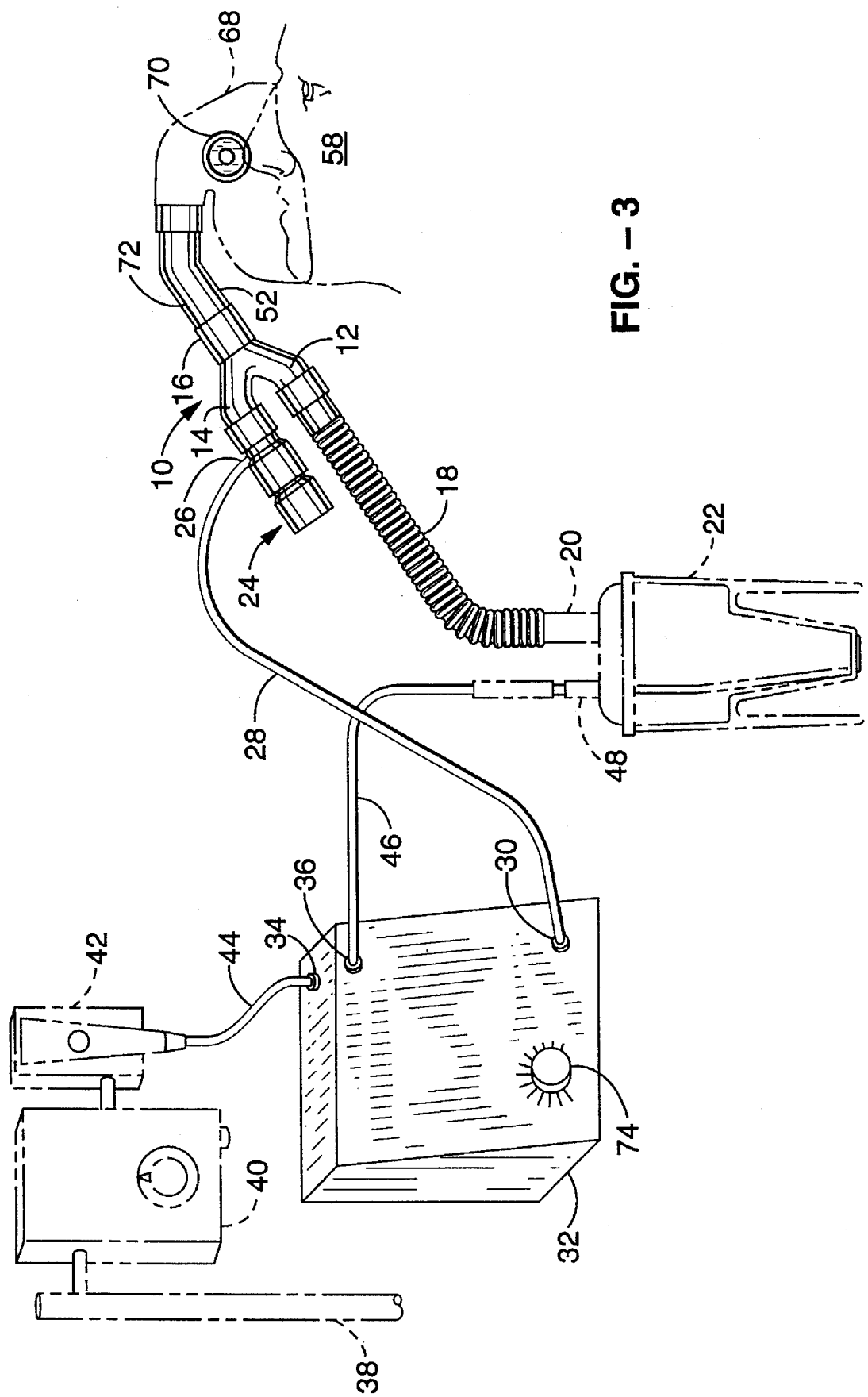

Referring also to FIG. 2, it can be seen that instead of using a mouthpiece 56 as shown in FIG. 1, a face mask 66 can be coupled to outlet 54. In this configuration, face mask 66 is a conventional face mask without an integral exhalation valve, and is substituted for mouthpiece 56. All other circuitry in the system remains the same. In the event that it is preferable or necessary to use a face mask which has an integral exhalation valve, the configuration shown in FIG. 3 can be employed. Shown is a face mask 68 having an integral exhalation valve 70 coupled to outlet 16 using a coupling tube 72. In this configuration, wye fitting 50 is eliminated as well as exhalation valve 60 and filter 64. Otherwise, all other circuitry remains the same. If exhalation gas filtering is desired, then the configuration of FIG. 2 should be employed. Alternatively, a secondary filter (not shown) could be connected to exhalation valve 70 with suitable means for coupling thereto.

Control unit 32 is an electro-mechanical controller or the like which synchronizes the aerosol delivery with the inhalation of patient 58. A charging control 74 is provided so that the charging time can be adjusted within a typical range of approximately 0.5 to 5.0 seconds. Preferably charging control 74 will have a dial resolution of approximately 100 milliseconds with an accuracy of plus or minus 15 percent of the setting. This will permit the user or therapist to adjust the charging time, which is initially set to approximate the inhalation time of the patient, to meet the patient's inspiration demand. Additionally, control unit 32 includes a pressure transducer (not shown) such as a MicroSwitch 163-PC-01-D-75 transducer or the like with temperature compensating circuity for sensing the pressure at pressure monitor input 30. The pressure transducer produces a one-volt signal output for a 2.54 cm-$H_2O$ pressure signal. The signal is amplified by a gain of approximately 10, and processed and compared against predetermined thresholds using conventional circuitry. If the threshold criteria is met, a normally closed pneumatic solenoid valve (not shown) contained within control unit 32 is activated to direct the flow of breathable gas to nebulizer 22.

In the preferred embodiment, activation of the charging solenoid by control unit 32 is dictated by two pressure threshold settings; an Nebulizer On Threshold (NOT) and a Hysteresis Threshold (HT). Breathable gas is permitted to flow to nebulizer 22 only when (a) the pressure sensed at pressure monitor input 30 falls below the NOT provided that (b) the pressure sensed at pressure monitor input 30 has exceeded the HT at any time subsequent to the previous charging operation. Preferably, the NOT is approximately 0.25 plus or minus 0.15 cm-$H_2O$ below atmospheric pressure and the HT is approximately 0.15 plus or minus 0.10 cm-$H_2O$ above atmospheric pressure. These threshold levels are a function of the resistance of valve 24, and can be varied without departing from the concepts presented herein. As can be seen, therefore, control unit 32 monitors the patient's inhalation and exhalation cycles and activates the solenoid valve in synchronization with the patient's breathing cycle. The control logic senses changes in pressure in relation to the NOT and HT so that charging occurs only when there has been a transition from a pressure above the NOT to a pressure below the NOT provided that the pressure previously exceeded the HT.

The gas supply to nebulizer 22 will shut off immediately upon expiration of the set charging time. In the event that the charging time has been set to a value which is shorter than the patient's inhalation cycle, the gas supply to nebulizer 22 will turn off upon completion of the set charging time. The charging time should then be adjusted to a value to more closely match the patient's inhalation cycle. In this way, aerosol contamination of the room environment will be prevented without the need for an exhalation filter. Furthermore, if contamination of the room environment from exhalation gas is not desired, an exhalation filter may be used and the present invention will significantly decrease resistance to exhalation flow experienced by the patient by eliminating the increase in pressure that would exist if the nebulizer was on during exhalation.

For home use, or for use where a pressured supply of breathable gas is not available, control unit 32 can include an internal compressor (not shown) for receiving and pressuring ambient air for delivery to nebulizer 22. In that event, in order to reduce wear on the compressor it is also desirable to provide a pressure sink to absorb pressure from the compressor when the solenoid valve is closed. The pressure sink (not shown) could be in the form of a reservoir, pressure relief orifice or the like located downstream of the compressor and upstream of the solenoid valve. In this way, the compressor will not be working against a complete flow obstruction when the solenoid valve is closed. Additionally, an intake filter (not shown) for filtering the ambient air could be included, as could water traps, air dryers, and the like.

Accordingly, it can be seen that this invention provides for delivery of medicinal aerosol to a patient's lungs efficiently and in controlled amounts, while at the same time minimizing or eliminating waste and contamination of the environment. Delivery of aerosol is automatically synchronized to patient inhalation by the device and, in the event that the mouthpiece is removed, the device will not reset and will not continue to deliver aerosol. Accordingly, it can be further seen that the present invention is also useful if the patient is interrupted and wishes to cease nebulizer treatment temporarily. In that event, the nebulizer employed will charge once during inhalation, and will not charge again until the device senses subsequent exhalation followed by inhalation. By monitoring the patient's inhalation and exhalation, aerosol is delivered based on actual patient demand and is not wasted as in prior devices. Furthermore, the present invention will significantly reduce the occlusion rate of an exhalation filter since aerosol will not be delivered during patient exhalation.

Although the description above contains many specificities, these should not be construed as limiting the scope of the invention but as merely providing illustrations of some of the presently preferred embodiments of this invention. Those skilled in the art will appreciate, for example, that wye fitting 10 and aerosol delivery conduit 18 could be of a unitary construction, as could the combination of wye fitting 10, aerosol delivery conduit 18, and wye fitting 50. Thus the scope of this invention should be determined by the appended claims and their legal equivalents.

I claim:

1. A breath actuated apparatus for on-demand delivery of medicinal aerosol produced by a nebulizer containing medicament aerosolized by a flow of breathable gas, comprising:

(a) a first wye, said first wye including first aerosol outlet means for delivering medicinal aerosol to a patient, said first wye including aerosol inlet means for receiving medicinal aerosol from a nebulizer, said first wye including air inlet means for receiving ambient air;

(b) a uni-directional inhalation valve coupled to said air inlet means;

(c) signalling means for providing an inhalation pressure signal representing inhalation of said patient and an exhalation pressure signal representing exhalation of said patient, said inhalation signal generated by said patient's inhalation airflow, said exhalation signal generated by said patient's exhalation airflow; and (d) control means for sensing the magnitude of said inhalation and exhalation signals, said control means being responsive to a threshold inhalation pressure followed by a threshold exhalation pressure to permit delivery of said breathable gas to a nebulizer only when said threshold inhalation pressure is followed by said threshold exhalation pressure.

2. An apparatus as recited in claim 1, further comprising an aerosol delivery conduit coupled to said aerosol inlet means.

3. An apparatus as recited in claim 1, further comprising:

(a) a second wye, said second wye including aerosol inlet means for receiving aerosol from said aerosol outlet means of said first wye, said second wye including aerosol outlet means for delivering aerosol to said patient, said second wye including exhalation gas outlet means for exhausting exhalation gases from said patient; and (b) a uni-directional exhalation valve coupled to said exhalation gas outlet means.

4. An apparatus as recited in claim 3, further comprising a filter coupled to said exhalation valve.

5. An apparatus for controlling delivery of medicinal aerosol to a patient for inhalation therapy, comprising:

(a) a first wye, said first wye including an aerosol inlet port, an air inlet port, and an aerosol outlet port, said aerosol inlet port including nebulizer coupling means for coupling to an aerosol nebulizer;

(b) a uni-directional inhalation valve coupled to said air inlet port;

(c) signalling means for providing an inhalation pressure signal representing inhalation of said patient and an exhalation pressure signal representing exhalation of said patient, said inhalation signal generated by said patient's inhalation airflow, said exhalation signal generated by said patient's exhalation airflow; and (d) control means for sensing the magnitude of said inhalation and exhalation signals, said control means being responsive to a threshold inhalation pressure followed by a threshold exhalation pressure to permit delivery of said breathable gas to a nebulizer only when said threshold inhalation pressure is followed by said threshold exhalation pressure.

6. An apparatus as recited in claim 5, wherein said nebulizer coupling means comprises an aerosol delivery conduit coupled to said aerosol inlet port.

7. An apparatus as recited in claim 5, further comprising:

(a) a second wye, said second wye including an aerosol inlet port coupled to said aerosol outlet port of said first wye, an aerosol outlet port, and an exhalation gas outlet port; and (b) a uni-directional exhalation valve coupled to said exhalation gas outlet port.

8. An apparatus as recited in claim 7, further comprising a filter coupled to said exhalation valve.

9. An apparatus as recited in claim 8, wherein said nebulizer coupling means comprises an aerosol delivery conduit coupled to said aerosol inlet port, and said apparatus further comprises an aerosol nebulizer, said aerosol nebulizer including an aerosol outlet port coupled to said aerosol delivery conduit, said nebulizer including a gas supply port coupled to said control means, said control means coupled to a supply of breathable gas.

10. An on-demand aerosol delivery apparatus for controlling amounts of medicinal aerosol delivered to a patient during inhalation therapy, comprising:

(a) a first wye, said first wye including an aerosol inlet port, an air inlet port, and an aerosol outlet port, said aerosol inlet port including nebulizer coupling means for coupling to an aerosol nebulizer;

(b) a uni-directional inhalation valve coupled to said air inlet port;

(c) an aerosol delivery conduit coupled to said aerosol inlet port, said aerosol deliver conduit including means for coupling to an aerosol nebulizer;

(d) signalling means for providing an inhalation pressure signal representing inhalation of said patient and an exhalation pressure signal representing exhalation of said patient, said inhalation signal generated by said patient's inhalation airflow, said exhalation signal generated by said patient's exhalation airflow; and (e) control means for sensing the magnitude of said inhalation and exhalation signals, said control means being responsive to a threshold inhalation pressure followed by a threshold exhalation pressure to permit delivery of said breathable gas to a nebulizer only when said threshold inhalation pressure is followed by said threshold exhalation pressure.

11. An apparatus as recited in claim 10, further comprising:

(a) a second wye, said second wye including an aerosol inlet port coupled to said aerosol outlet port of said first wye, an aerosol outlet port, and an exhalation gas outlet port; and (b) a uni-directional exhalation valve coupled to said exhalation gas outlet port.

12. An apparatus as recited in claim 11, further comprising a filter coupled to said exhalation valve.

* * * * *